(12) United States Patent
Golan et al.

(10) Patent No.: US 6,509,553 B2
(45) Date of Patent: Jan. 21, 2003

(54) METHOD AND APPARATUS FOR PROVIDING AN INDICATION OF THE COMPOSITION OF A FLUID PARTICULARLY USEFUL IN HEAT PUMPS AND VAPORIZERS

(75) Inventors: Gady Golan, Hod Hasharon (IL); Zeev Shavit, Doar Na Misgav (IL)

(73) Assignee: A.T.C.T. Advanced Thermal Chips Technologies Ltd., Tel Aviv (IL)

(*) Notice: Subject to any disclaimer, the term of this patent is extended or adjusted under 35 U.S.C. 154(b) by 25 days.

(21) Appl. No.: 09/791,684

(22) Filed: Feb. 26, 2001

(65) Prior Publication Data

US 2002/0144994 A1 Oct. 10, 2002

Related U.S. Application Data (60) Provisional application No. 60/229,734, filed on Sep. 5, 2000.

(51) Int. Cl.[7] .............................. H05B 1/02; G01F 1/68; G01N 25/00
(52) U.S. Cl. .................... 219/505; 73/204.11; 73/61.46
(58) Field of Search ................................. 219/499, 504, 219/505, 509, 510; 73/1.02, 1.16, 1.73, 204.11, 204.12, 204.15, 204.17, 204.25, 204.26, 204.27, 54.42, 61.43, 61.46

(56) References Cited

U.S. PATENT DOCUMENTS

| | | | | |
|---|---|---|---|---|
| 3,864,969 A | * | 2/1975 | Smith, Jr. ................... | 374/136 |
| 3,890,588 A | * | 6/1975 | Kanaya et al. ............... | 338/28 |
| 3,891,391 A | * | 6/1975 | Boone ..................... | 73/204.18 |
| 4,319,483 A | * | 3/1982 | Durham et al. .......... | 73/204.15 |
| 4,575,260 A | * | 3/1986 | Young ........................ | 374/136 |
| 5,031,126 A | * | 7/1991 | McCulloch et al. ........ | 340/622 |
| 5,069,066 A | * | 12/1991 | Djorup ..................... | 73/204.15 |
| 5,112,136 A | * | 5/1992 | Sakuma et al. ............ | 374/110 |
| 5,335,513 A | * | 8/1994 | Campbell et al. ............ | 374/16 |
| 6,293,114 B1 | * | 9/2001 | Kamemoto ................... | 62/126 |

* cited by examiner

Primary Examiner—Sang Paik
(74) Attorney, Agent, or Firm—G. E. Ehrlich Ltd.

(57) ABSTRACT

A method and apparatus for providing an indication of the composition of an examined fluid by using an electrical resistor, particularly a positive temperature coefficient thermistor, for measuring the thermal conductivity of the examined fluid with the known thermal conductivity of different fluid compositions. The method and apparatus are particularly described for indicating the relative proportions of a working fluid in the liquid and vapor phases in one or more stages of a heat pump. Another described application is for indicating the liquid level in a liquid vaporizer.

28 Claims, 6 Drawing Sheets

METHOD AND APPARATUS FOR PROVIDING AN INDICATION OF THE COMPOSITION OF A FLUID PARTICULARLY USEFUL IN HEAT PUMPS AND VAPORIZERS

RELATED APPLICATION

The present application is related to Provisional Application No. 60/229,734, filed Sep. 5, 2000, and claims the priority date of that application.

FIELD AND BACKGROUND OF THE INVENTION

The present invention relates to a method and apparatus for providing an indication of the composition of an examined fluid. The invention is particularly useful in a heat pump for indicating the physical, or phase, composition of the working fluid (i.e., the relative proportions of the working fluid in the liquid and vapor phases) at one or more stages of the heat pump cycle. Another application is for indicating the liquid level in a vaporizer. The invention is therefore described below particularly with respect to these two applications, but it will be appreciated that the invention is useful in many other applications.

Heat pumps are widely used for heating and/or cooling purposes. They include a phase-changing working fluid driven through a closed loop including a compressor, a condenser, an expansion valve, and an evaporator. The proper and efficient operation of such a heat pump depends to a considerable degree on the ability to control the physical composition of the working fluid (i.e., the relative proportions in the liquid and vapor phases) at the different stages of the closed loop cycle, particularly at the inlet to the evaporator, and at the outlet from the evaporator. Thus, if the working fluid is not completely in the liquid phase at the inlet to the evaporator, and not completely in the vapor phase at the outlet from the evaporator, the overall efficiency of the heat pump cycle could be significantly lowered; moreover, the loss of working fluid by leakage could go undetected.

Many Vapor Cycle Systems (VCS) use pressure sensors to measure the pressure at the various stages of the cycle, but pressure sensors tend to provide false alarms at cold conditions below 0° C., or at low heat load conditions. Sometimes, in order to overcome false alarms, the system may include a temperature valve that disconnects the low pressure information at low temperatures, to thereby avoid a false alarm. This solution is frequently applied to systems used in avionics, but such a solution does not solve the problem in case of a real leak.

There are many other areas where it is highly desirable to be able to provide an indication of the composition or phase content of an examined fluid in a quick and simple manner. One such other application is for indicating the liquid level in a vaporizer outlet. Other possible applications would be for identifying liquid flow in an oil system, water flow in an irrigation system, liquid coolant flow in a cooling system, and other liquid, gas or vapor flow systems.

OBJECTS AND BRIEF SUMMARY OF THE PRESENT INVENTION

An important object of the present invention is to provide a novel method, and also a novel apparatus, for indicating the composition of a fluid in a quick and facile manner. Another object of the invention is to provide a novel method and apparatus for indicating the relative proportions of a working fluid that are in the liquid and vapor phases in one or more stages of a heat pump. A further object is to provide a novel method and apparatus for indicating the liquid level in a vaporizer.

According to one aspect of the present invention, the invention relates to a method of providing an indication of the composition of an examined fluid, comprising:

immersing an electrical resistor within the examined fluid; applying electrical current through the electrical resistor to heat it to a temperature above that of the examined fluid; controlling the electrical current applied through the electrical resistor to maintain the electrical resistor substantially at a predetermined temperature while the electrical resistor is immersed in the fluid; measuring the electrical current applied through the electrical resistor to maintain it substantially at the predetermined temperature, to provide a measurement of the rate of heat dissipation from the electrical resistor via the examined fluid and, thereby, a measurement of the thermal conductivity of the examined fluid; and comparing the measured thermal conductivity of the examined fluid with the known thermal conductivities of different fluid compositions to provide an indication of the composition of the examined fluid.

According to an important preferred feature of the present invention, the electrical resistor is a positive temperature coefficient (PTC) thermistor. Such thermistors can be constructed by known doping and sintering processes to have a maximum predetermined temperature irrespective of the power supplied to the thermistor, thereby obviating the need for additional controls or temperature sensors when used as the electrical resistor immersed in the fluid to be examined in accordance with the present invention. Many other important advantages in the use of such thermistors are described below.

The invention is particularly useful where the fluid is examined for its physical composition, e.g., to determined the relative proportions thereof in the liquid and gaseous phases. One particular application of the invention is in the examination of a phase-changing working fluid in one or more stages of a heat pump for indicating the proportions of the working fluid in the liquid and vapor phases at the respective stage of the heat pump cycle. The results of the examination of the working fluid may be used for optimizing the heat pump cycle, as well as for detecting leakage of working fluid, etc.

According to a second described preferred embodiment, the fluid is a liquid in a vaporizer inlet, and is examined at one or more levels therein to indicate the vapor content in the vaporizer outlet.

While the invention is particularly useful, and is therefore described below, for indicating the physical composition of a fluid (e.g., the relative proportions in the liquid and vapor states), the invention may also be used for determining the chemical composition of a fluid, (e.g., a mixture of different fluids having different thermal properties) in which case the measured thermal property of the examined fluid would be compared with the known thermal property of fluids of different compositions to provide an indication of the chemical composition of the examined fluid.

When the invention is used for indicating either the physical composition or the chemical composition of a fluid, the fluid should of course be non-flowing, or flowing at a known velocity, so that the measured thermal conductivity can be compared to the known thermal property of other fluids under the same velocity conditions. Once the fluid has been examined to provide an indication of its composition, it may then be examined while flowing at an unknown velocity also to indicate its velocity.

According to another aspect, the invention also relates to apparatus for providing an indication of the composition of an examined fluid, comprising: an electrical resistor having a mounting device for mounting the electrical resistor immersed in the fluid to be examined; a power supply for supplying electrical current to the electrical resistor to heat it to a temperature above that of the examined fluid; and a processor for: (a) controlling the heating current applied to the electrical resistor to maintain the electrical resistor substantially at a predetermined temperature; (b) measuring the electrical current applied to the electrical resistor to maintain it substantially at the predetermined temperature; and (c) producing an output, based on the measured electrical current, indicating the composition of the examined fluid. Particularly good results are obtained, as indicated above and as described more particularly below, when the electrical resistor is a positive temperature coefficient (PTC) thermistor.

Further features and advantages of the invention will be apparent from the description below.

BRIEF DESCRIPTION OF THE DRAWINGS

The invention is herein described, by way of example only, with reference to the accompanying drawings, wherein.

BRIEF DESCRIPTION OF THE METHOD

The present invention is based on the fact that the rate of heat dissipation produced by a fluid with respect to an electrical heater immersed in the fluid is related to the thermal properties of the fluid. Measuring the rate of heat dissipation has previously been used to provide an indication of the rate of flow of the fluid. The present invention utilizes the rate of heat dissipation to provide an indication of the composition of the fluid. In the preferred embodiments of the invention described below, the method is used to provide an indication of the physical composition of the fluid, particularly the relative proportions of the fluid in the liquid and vapor states. The invention, however, could also be advantageously used for providing an indication of the species composition of the fluid.

The electrical heater could, theoretically, be any type of electrical heater wherein the rate of heat dissipation is measured by controlling the electrical current through the electrical resistor to maintain it substantially at a predetermined temperature while the resistor is immersed in the fluid, and measuring the electrical current through the electrical resistor to maintain it substantially at the predetermined temperature. However, as indicated earlier, particularly good results are obtainable when the electrical resistor is a positive temperature coefficient (PTC) thermistor. Such a thermistor, when operating at a preset maximum temperature, produces a current flow directly related to the thermal load, in this case, to the heat dissipation rate produced by the fluid in which the thermistor is immersed. The dissipation of the heat by the fluid tends to cool the thermistor, which thereby requires it to draw more current in order to maintain its preset maximum temperature.

Thus, when a PTC thermistor sensor is immersed in a fluid and heated to its preset maximum temperature (which is above the temperature of the fluid), and is maintained at that temperature, the heat load (Q) on the sensor is equal to:

$$Q = U^*(Ts-Tf), \qquad (1)$$

Where: U is the heat transfer coefficient (h multiplied by the sensor's surface area); Ts is the sensor's temperature; and Tf is the fluid temperature.

The invention is particularly useful in indicating the relative proportions of a working fluid in the liquid phase and in the gas phase at various locations in a Vapor Cycle System (VCS), such as a heat pump for cooling or heating air. In such a system, the heat transfer coefficient (U) for the liquid phase is at least ten times higher than that of the gas phase, whereas the temperature difference (Ts–Tf) usually does not vary more than 5 times between the lowest and highest temperature difference level. The sensor temperature (Ts) remains relatively constant within a range of 5° C. It is therefore expected that the sensor's heat-load, which is exposed to the gas flow, will be at least 5 times lower than that of the liquid flow, even if the fluid temperature Tf varies maximally as expected.

Usually, in Vapor Cycle Systems (VCS), the range of the fluid temperature (Tf), measured after the thermal expansion valve (TXV), is between 0° C. to 25° C. during a normal operation. In case of a leakage with no refrigerant liquid in the system, the fluid temperature (Tf) moves towards the ambient temperature. The power dissipation of the PTC sensor (Ps) is equal to the heat load (Q): therefore, for a constant voltage power supply, the sensor's resistance Rs varies with Q, as:

$$R_s = V^2/P \qquad (2)$$

and: $P = Q$; therefore:

$$R_s = \frac{V^2}{U \cdot (Ts - Tf)}$$

The sensor's current consumption, Is, changes accordingly; thus:

$$Is = \frac{V}{U \cdot (Ts - Tf)]} \quad (3)$$

In order to assure a proper operation, the temperature of the PTC thermistor sensor Ts, should be kept always higher than Tf (Ts>Tf). Also, the sensor should be manufactured small enough to minimize bulk heating of the cold fluid. Typical dissipating power of a PTC thermal chip is kept less than one watt.

The PTC thermistor sensor can thus be used for sensing the rate of heat dissipation, and thereby the thermal conductivity, of the fluid in which the thermistor is immersed when the fluid is either relatively stationary, or moving at a known velocity.

It will also be appreciated that, when the composition of the examined fluid has been determined in the above-described manner, the same technique can also be used for determining the rate of flow of the fluid.

Thus, where fluid flow rates (mf) are to be measured, Tf is measured and Ts is expected to change within 10° C. Then measuring Is produces a measurement of the fluid flow rate (mf) since, according to e.g., (3) above:

$$Is = f(Tf, mf) \quad (4)$$

DESCRIPTION OF PREFERRED EMBODIMENTS

The preferred embodiments of the invention described below utilize a PTC thermistor sensor as the electrical resistor immersed within the fluid to be examined. As described above, using such a thermistor for the sensor obviates the need for additional controls or temperature sensors since the temperature of the sensor does not rise significantly above its maximum temperature irrespective of the voltage applied to it. A preferred PTC thermistor is one made of barium titanate, since this material is characterized by a very high resistance to corrosion and a relatively low hazard to explosion when exposed to certain gases.

Figure 1:
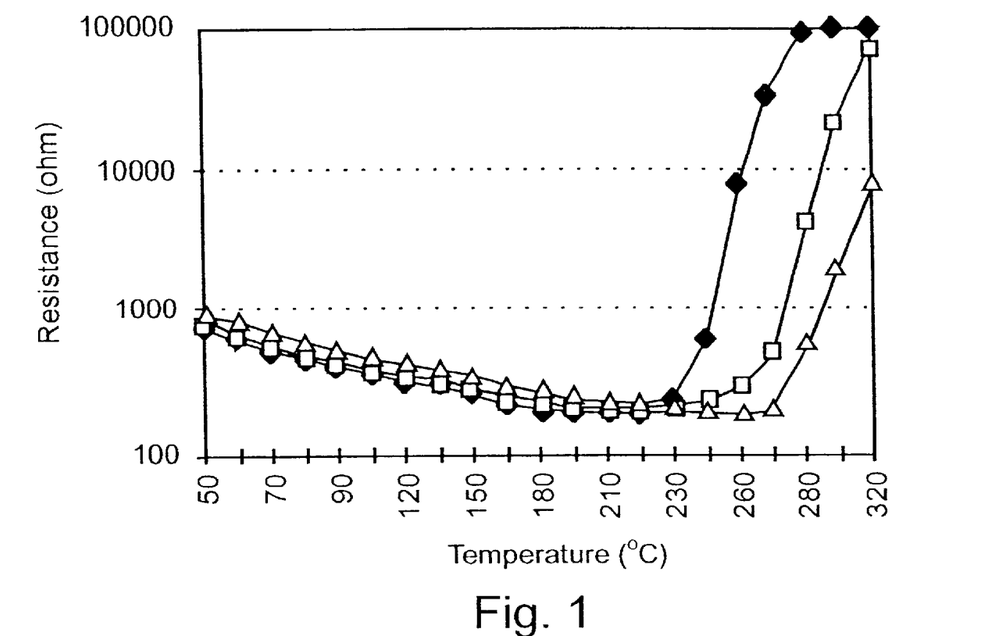
FIG. 1 are curves illustrating the temperature—resistance relationship of three typical positive temperature coefficient (PTC) thermistors.

FIG. 1 includes curves illustrating the temperature-resistance relationship of three typical PTC thermistor, wherein it will be seen that at a preset temperature, depending on the composition of the thermistor, the resistance grows abruptly virtually to infinity.

Figure 2:
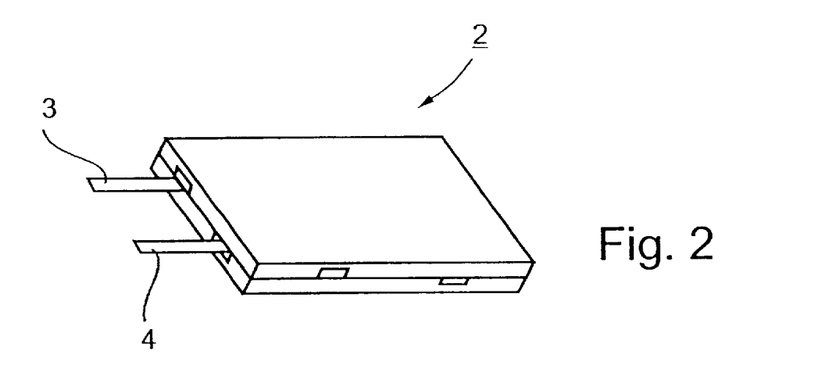
FIG. 2 is a three-dimensional magnified view illustrating one form of PTC thermistor particularly useful as a fluid sensor in the present invention.

FIG. 2 is a three-dimensional view illustrating one form of sensor unit, generally designated 2, including one or more such thermistors. The thermistor is preferably of barium titanate produced by a sintering process and doped according to the desired maximum temperature, enclosed within a housing of thermally-conductive, electrically-insulating material, such as $AL_2O_3$, and is provided with electrodes 3, 4, for connection to the electrical supply. The outer surfaces of the sensor unit 2 are preferably coated with a conductive metal, such as aluminum, in order to provide good thermal contact with the fluid in which the sensor is immersed.

Since such PTC thermistor sensors are well known and commercially available, further details of its construction are not set forth herein.

Figure 3:
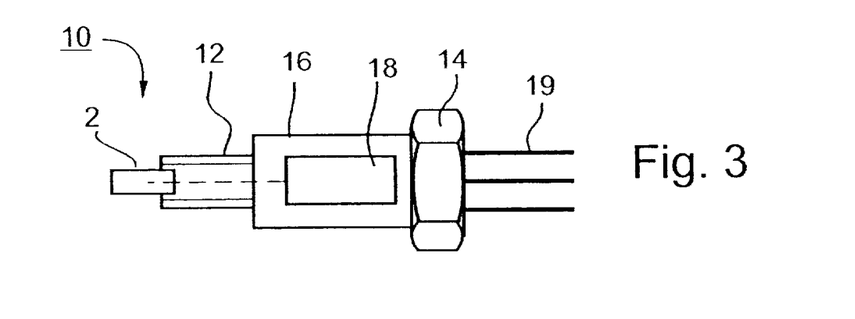
FIG. 3 illustrates one form of sensor constructed in accordance with the present invention incorporating a PTC thermistor for monitoring the physical composition of a fluid to be examined.

FIG. 3 illustrates a sensor assembly for mounting the sensor unit 2 to a housing containing the fluid to be examined. The housing may be, for example, a container containing the fluid to be examined, or may be a conduit through which the fluid to be examined flows. In either case, the sensor assembly illustrated in FIG. 3, and therein designated 10, mounts the sensor unit 2 in the housing such that the sensor unit is completely immersed within the fluid in the housing.

Thus, the sensor assembly 10 illustrated in FIG. 3 includes the sensor unit 2 at one end 12 carried by a fitting 12, and a mounting device 14 at the opposite end, such as a threaded member, for mounting the sensor unit 2. The sensor assembly 10 further includes a housing 16 for the sensor circuitry 18 (as illustrated in FIG. 6) and output leads 19 for outputting the signal from the sensor circuit 18.

As described below with respect to FIG. 6, the sensor circuitry 18 includes two sensor units: one sensor unit is exposed to the fluid being examined, whereas the other sensor unit serves as a reference and is not exposed to the fluid being examined.

Figure 4:
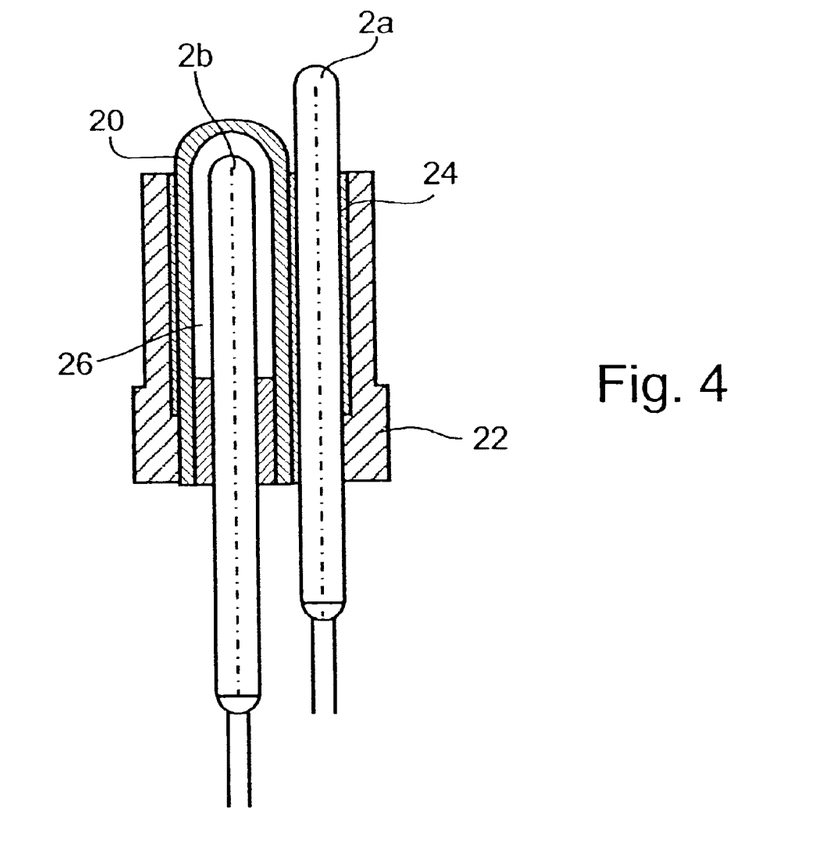
FIGS. 4 and 5 are enlarged sectional and end views, respectively, more particularly illustrating the structure of the sensor elements in the sensor of FIG. 3, FIG. 4 being a sectional view along line IV—IV of FIG. 5.
Figure 5:
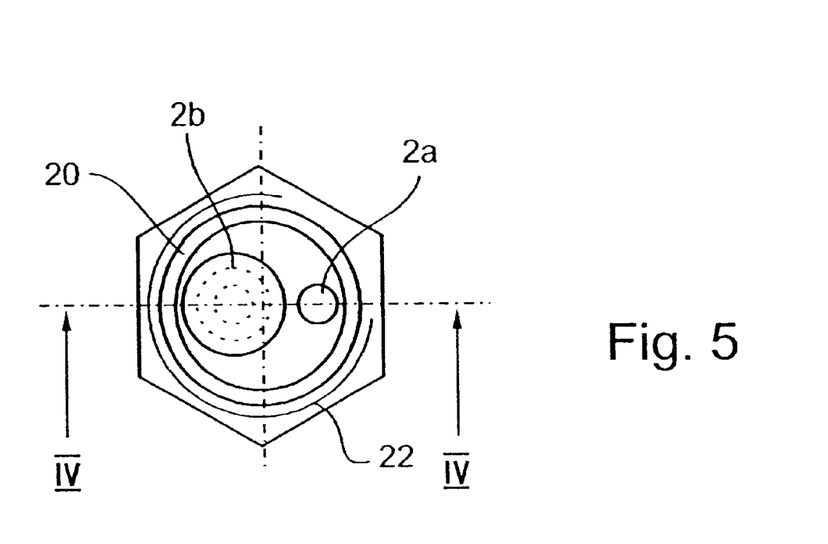

FIGS. 4 and 5 illustrate such a sensor assembly, in which one sensor unit 2a is left bare so as to be exposed to the fluid being examined, whereas the other sensor unit 2b is enclosed within a metal housing 20 so as to be shielded from the fluid being examined. Both are carried by a plug mounting device 22. The exposed sensor unit 2a is embedded within a sealing material 24, except for its outer end which is exposed to the fluid being examined. The metal housing 20 enclosing the reference sensor unit 2b also includes a liquid thermally insulating material 26.

Figure 6:
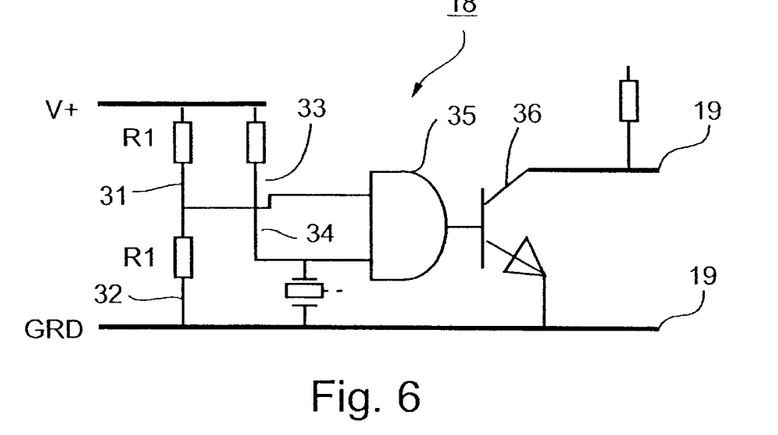
FIG. 6 is a circuit diagram illustrating the circuitry included in the sensor of FIGS. 3–5.

The electrical circuit 18 within housing 16 is more particularly illustrated in FIG. 6. The circuit is in the form of a bridge having two legs 31, 32 including a resistor R1, a third leg 33 including a reference PTC thermistor sensor 2b, and a fourth leg 34 including the PTC thermistor sensor 2a to be immersed in the fluid being examined. Thus, reference sensor 2b should be identical to the measuring sensor 2a, but is not immersed in the fluid being examined. Sensor 2a thus provides a measurement of the heat dissipation, and thereby of the thermal conductivity, of the fluid being examined.

The electrical circuit 18 within the sensor assembly (10, FIG. 3, or 20, FIGS. 4, 5) further includes a comparator 35 having a first input 35a connected to the juncture between the two resistors R1 of the first two legs 31, 32, and a second input 35b connected to the juncture of the two PTC thermistor sensors 2a, 2b in legs 33, 34. The output from the comparator 35 is amplified by a transistor 36 before appearing in the output leads 19.

Figure 7:
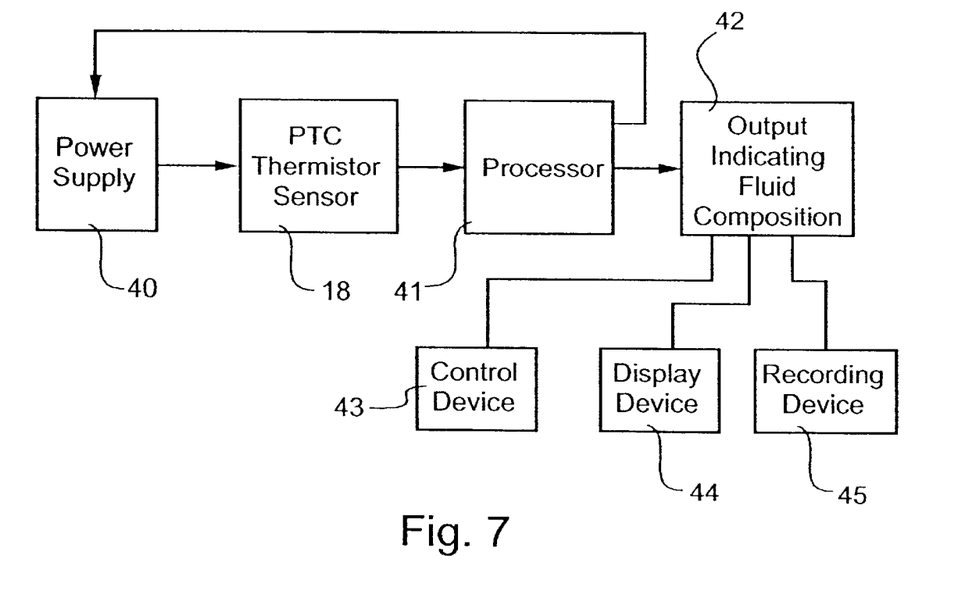
FIG. 7 is a block diagram illustrating the overall apparatus including the PTC thermistor sensor of FIGS. 3–6 for examining a fluid to indicate its composition.

FIG. 7 is a block diagram illustrating the overall apparatus including the PTC thermistor sensor circuit 18 included in the sensor assembly 10 (or 20). Thus, as shown in FIG. 7, the apparatus includes a power supply 40 for supplying electrical current to the two thermistor sensors 2a, 2b of the thermistor sensor circuit 18; and a processor 41 for controlling the power supply 40 to control the heating current applied to the two thermistor sensors in order to maintain them substantially at their respective predetermined temperatures. Processor 41 also measures the electrical current applied to thermistor sensor 2a to maintain it substantially at its predetermined temperature, and produces an output, shown at 42, indicating the composition of the examined fluid in which thermistor sensor 2a was immersed. As briefly described earlier, this output is produced by comparing the measured thermal conductivity of the examined fluid with the known thermal properties of different fluid compositions to thereby provide an indication of the composition of the examined fluid.

As shown in FIG. 7, the output from processor 41 indicating the fluid composition may be used for control purposes, as shown at 43, for display purposes as shown at 44, or for record purposes as shown at 45.

Figure 8:
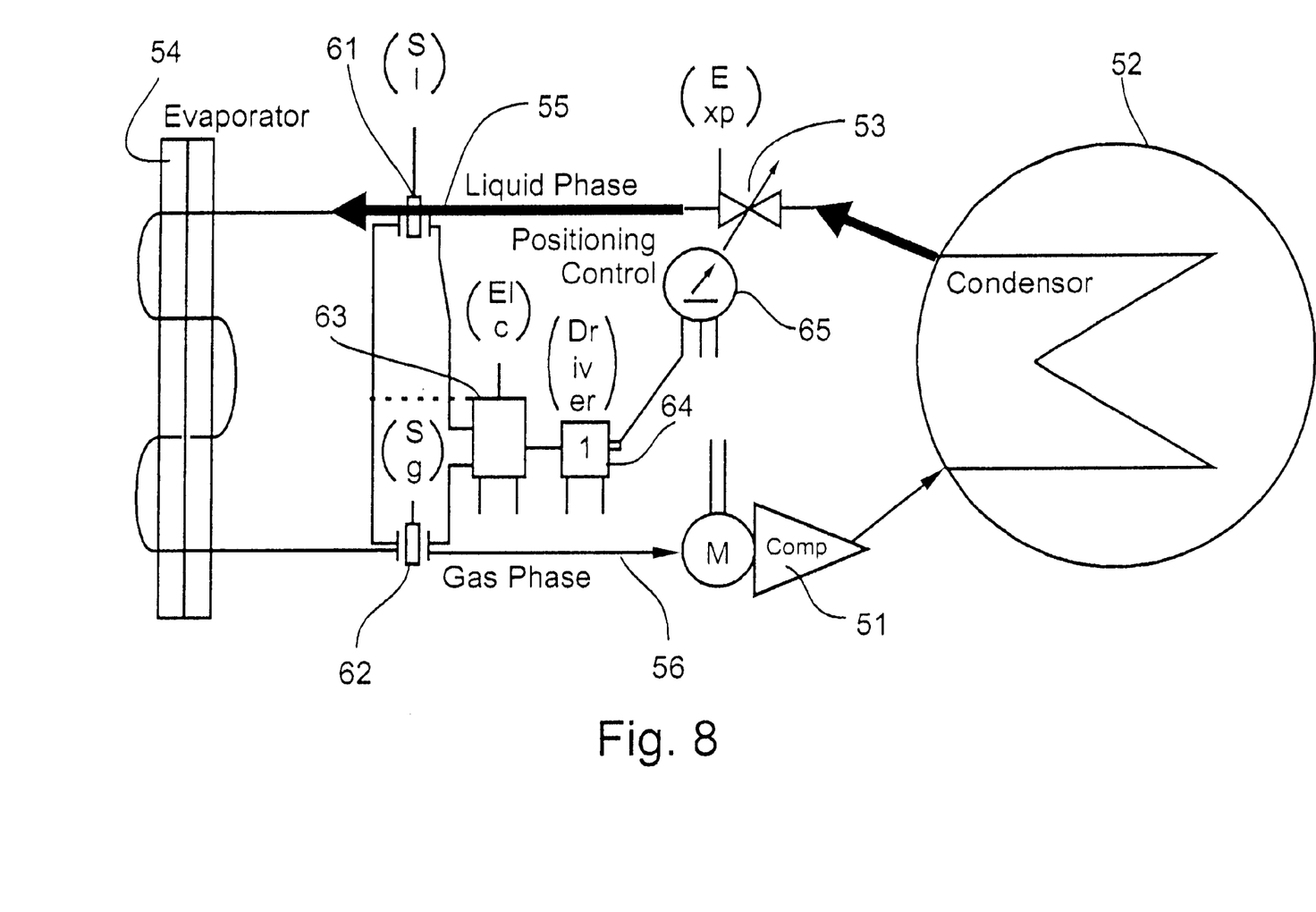
FIG. 8 is a diagram illustrating one preferred embodiment of the invention, namely for detecting the physical composition of a working fluid (i.e., the relative proportions of the working fluid in the liquid and vapor states) in different stages of a heat pump cycle in order to optimize the cycle as well as to indicate possible leakage of the working fluid.

FIG. 8 illustrates the invention implemented in a Vapor Cycle System (VCS) of a heat pump, for detecting the physical composition of the working fluid, i.e., the relative proportions of the working fluid in the liquid and vapor phases in particular stages of the VCS cycle.

The Vapor Cycle System (VCS) illustrated in FIG. 8 includes a phase-changing working fluid driven through a closed loop, comprising a compressor 51, a condenser 52, an expansion valve 53, and an evaporator 54. The expansion valve 53 is connected via a liquid phase line 55 to the inlet of the evaporator 54; and the outlet from the evaporator is connected via a gas phase line 57 to the compressor 51.

FIG. 8 illustrates a first PTC thermistor sensor 61 in the liquid phase line 55, to provide an indication of the state of the working fluid in the liquid phase line 55 between the expansion valve 53 and the inlet to the evaporator 54. The system in FIG. 6 includes a second PTC thermistor sensor 62 in the gas phase line 56 to provide an indication of the state of the working fluid fed from the outlet of the evaporator 54 to the compressor 51. Thus, proper operation of the VCS at optimum efficiency requires that the working fluid be substantially completely in the liquid phase at the location where examined by the PTC thermistor sensor 61, and be substantially completely in the vapor state where examined by the PTC thermistor sensor 62. Such sensors can also be used to provide an indication of whether working fluid is leaking from the VCS, and where.

The system illustrated in FIG. 8 further includes a processor 63 for controlling the power supply supplying the electrical current to the two thermistor sensors 61, 62 to maintain them substantially at their respective predetermined temperatures, and thereby to enable them to measure the heat conductivity of the working fluid at the respective stage of the cycle. Processor 63 also measures the electrical current applied to the thermistor sensors 61, 62 to maintain them substantially at their respective maximum temperatures, such that the current supplied to the thermistor sensors will provide an indication of the physical composition (i.e., its liquid/vapor state) of the working fluid at the respective location.

In the system illustrated in FIG. 8, the microprocessor 63 also produces an output which is used for controlling the expansion valve 53 in response to the measurements made by the thermistor sensor 61. Thus, processor 63 produces an output to a driver 64 which drives a position controller 65 coupled to the expansion valve 33 to control the latter valve.

Figure 9:
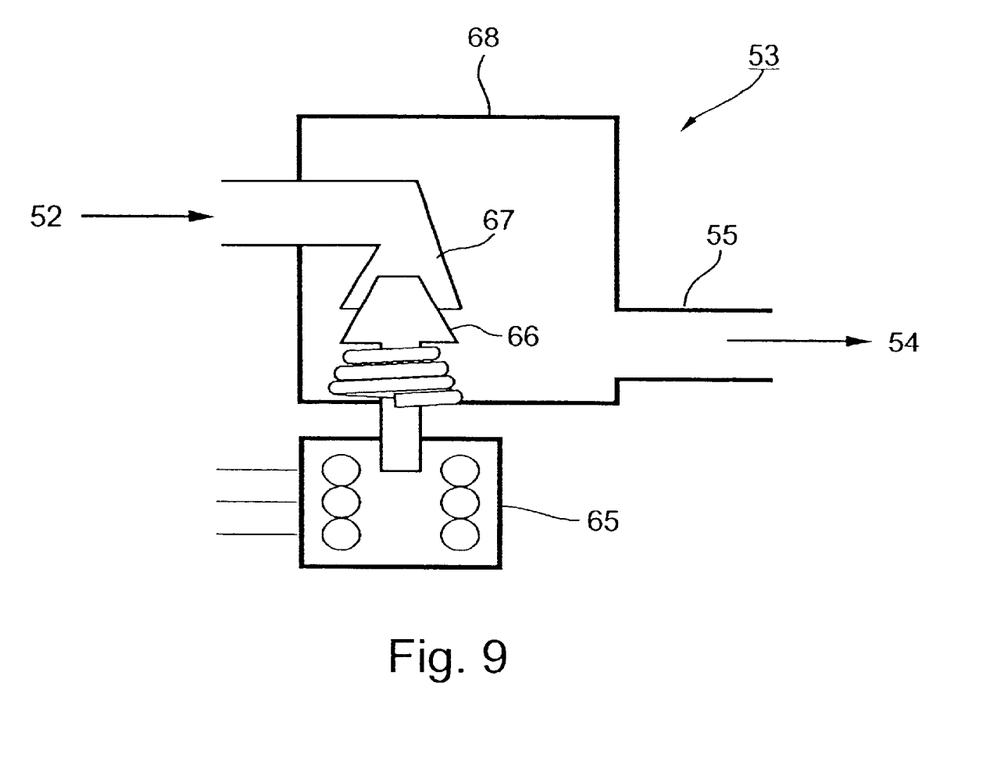
FIG. 9 is a diagram illustrating one manner of controlling the expansion valve in the heat pump cycle of FIG. 8.

FIG. 9 more particularly illustrates one possible manner in which the expansion valve 53 may be controlled by the processor 63. Thus, as shown in FIG. 9, the valve driver 65 is a step motor which drives a conical valve head 66 with respect to a complementary-shaped conical passageway 67 within the housing 68 of the expansion valve 53. Passageway 67 is coupled to the outlet of condensor 52, whereas the interior of housing 68 is coupled to the liquid phase line 55 leading to the inlet of the evaporator 54. Accordingly, the output from the processor 63 is utilized, via the driver circuit 64 and the step motor 65, to control the spacing between the conical valve head 66 and the passageway 67 within the expansion valve 53, and thereby the degree of expansion of the fluid (liquid) fed from the condenser 52 via the liquid phase line 55 to the inlet of evaporator 54.

Other expansion control valves can be used, e.g., according to the known solenoid PW 19 system or other systems. For example, the system may be used with thermal expansion valve with a refrigerant pressure bulb, in which the bulb temperature is controlled by a small thermoelectric component by a controller such as shown at 64 in FIG. 8.

Figure 10:
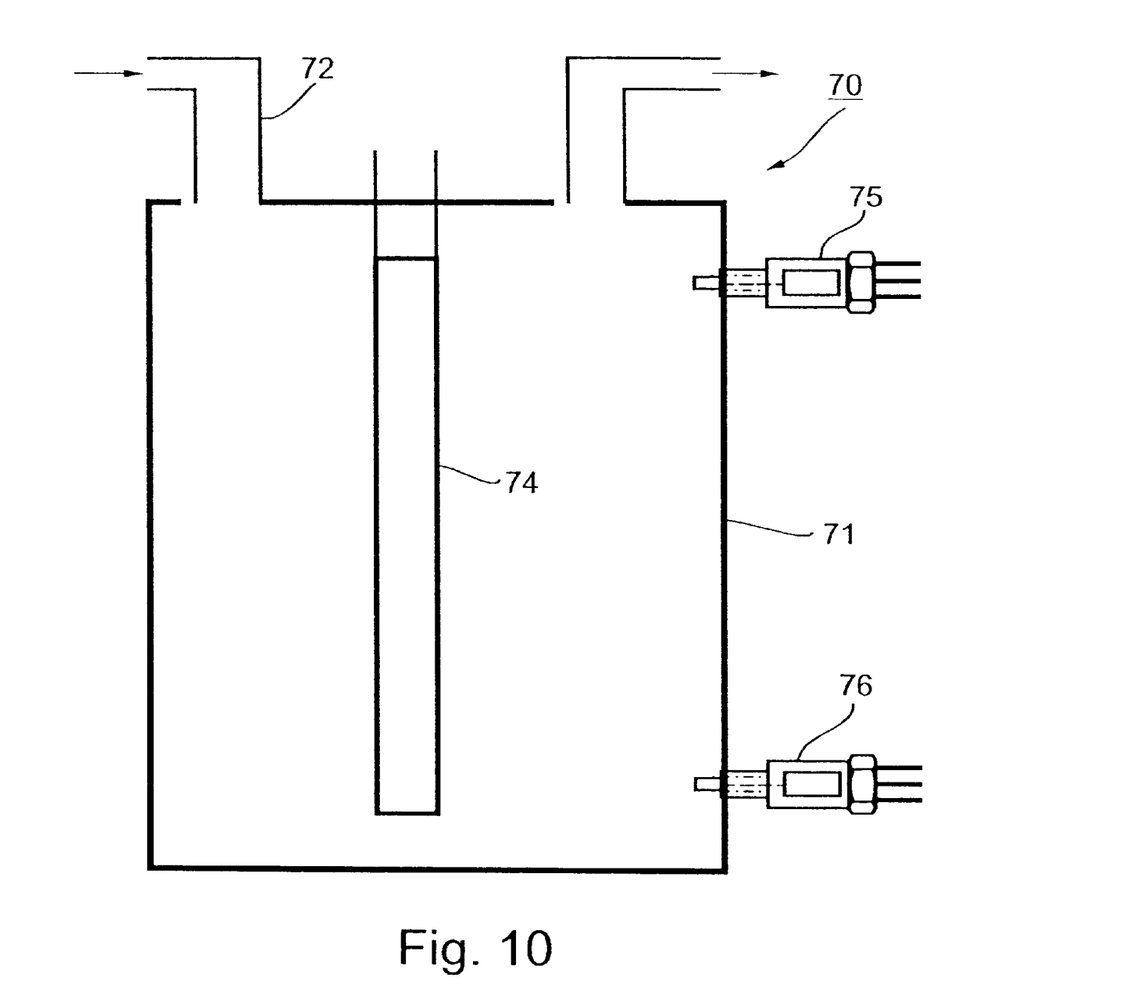
FIG. 10 illustrates a second embodiment of the invention, as applied for indicating the liquid level in a vaporizer.

FIG. 10 illustrates the invention implemented in a liquid vaporizer, generally designated 70, to provide an indication of the liquid level within the vaporizer. Thus, as shown in FIG. 10, the vaporizer includes a container 71 having a liquid (e.g., water) inlet 72 and a vapor outlet 73. The liquid within the container is heated by a heater 74 immersible in the liquid. Preferably, the heater 74 is also a PTC thermistor, but may be any other type of electrical heater commonly used for heating water or other liquids.

In accordance with the present invention, the vaporizer illustrated in FIG. 10 includes a PTC thermistor sensor assembly 75 at the desired liquid high-level location within container 70, and a second PTC thermistor sensor assembly 76 at the desired low-level location. Each of the sensor assemblies 75, 76 may be of the construction described above with respect to FIGS. 3–6. Their outputs may be used for signaling purposes or for control purposes. For example, the output of the PTC thermistor sensor assembly 75 may be used for controlling the inflow of the liquid via the inlet 72 to maintain the liquid level at that location of the container; whereas the output of the PTC thermistor assembly 76 may be used for sounding an alarm and/or for disconnecting the power supply to the heater 74 in case of the level of the liquid drops below that level of the container.

While the invention has been described with respect to several preferred embodiments, it will be appreciated that these are set forther merely for purposes of example, and that the invention could be used in many other applications. For example, it can be used in a device examining the air outside of an aircraft in order to provice a warning against condensation after the aircraft penetrates a high moisture atmosphere. Another possible application would be to examine the fluid at the cooling outlets of turbines, to avoid an increase in its RPM. Thus, impingement if liquid droplets on the PTC thermistor sensor would immediately increase the thermal load on the thermal sensor, manifested by an increase in its current, such that positioning the sensor in a specific loction, e.g., in a small diffuser which reduces local pressure, will produce an alarm signal right before penetrating a condensation condition in the main stream.

The invention could also be used for indicating the chemcial composition of a fluid, by comparing its measured thermal conductivity with the known thermal conductivities of varous known materials. Also, once the composition of a material is indicated in the manner described above, the invention could also be used for measuring the flow velocity of that material.

Many other applications of the invention will be apparent.

What is claimed is:

1. A method of providing an indication of the composition of an examined fluid, comprising:

immersing an electrical resistor within the examined fluid;

applying electrical current through the electrical resistor to heat it to a temperature above that of the examined fluid;

controlling the electrical current applied through the electrical resistor to maintain the electrical resistor substantially at a predetermined temperature while the electrical resistor is immersed in said fluid;

measuring the electrical current applied through the electrical resistor to maintain it substantially at said predetermined temperature, to provide a measurement of the rate of heat dissipation from the electrical resistor via said examined fluid and, thereby, a measurement of the thermal conductivity of the examined fluid;

and comparing the measured thermal conductivity of the examined fluid with the known thermal conductivities of different fluid compositions to provide an indication of the composition of the examined fluid.

2. The method according to claim 1, wherein said electrical resistor is a positive temperature coefficient (PTC) thermistor.

3. The method according to claim 1, wherein the examined fluid is examined for its physical composition with respect to the relative proportions thereof in the liquid and gaseous phases.

4. The method according to claim 1, wherein the examined fluid is a phase-changing working fluid driven through a closed-loop cycle in a heat pump, and is examined in at least one stage of the heat pump cycle for indicating the proportions of the working fluid in the liquid and vapor phases at the respective stage.

5. The method according to claim 4, wherein said heat pump includes an evaporator, a condenser, an expansion valve between the condenser and the evaporator, and a compressor between the evaporator and the condenser; and wherein the working fluid is examined between the expansion valve and the evaporator.

6. The method according to claim 5, wherein the results of said examination of the working fluid are used for controlling said expansion valve.

7. The method according to claim 5, wherein the working fluid is also examined between the evaporator and the compressor.

8. The method according to claim 1, wherein the examined fluid is a liquid in a vaporizer, and is examined at least one level therein to indicate the liquid level in the vaporizer.

9. The method according to claim 1, wherein the examined fluid is examined for its chemical composition.

10. The method according to claim 1, wherein the fluid is first examined while non-flowing or flowing at a known velocity to indicate its composition, and then is examined while flowing at an unknown velocity to indicate its velocity.

11. A method of providing an indication of the composition of an examined fluid, comprising:

immersing within the examined fluid a positive temperature coefficient (PTC) thermistor having a predetermined maximum temperature above the temperature of the examined fluid;

applying electrical current through the thermistor to heat it to, and to maintain it, at said predetermined maximum temperature;

measuring the current applied through the PTC thermistor, to maintain the thermistor at said maximum predetermined temperature such as to provide thereby a measurement of the thermal conductivity of the examined fluid;

and comparing the measured thermal conductivity of the examined fluid with the known thermal conductivities of different fluid compositions to provide an indication of the composition of the examined fluid.

12. The method according to claim 11, wherein the examined fluid is a phase-changing working fluid drive through a closed-loop cycle in a heat pump, and is examined in at least one stage of the heat pump cycle for indicating the proportions of the working fluid in the liquid and vapor phases at the respective stage.

13. The method according to claim 12, wherein said heat pump includes an evaporator, a condenser, an expansion valve between the condenser and the evaporator, and a compressor between the evaporator and the condenser; and wherein the working fluid is examined between the expansion valve and the evaporator.

14. The method according to claim 13, wherein the results of said examination of the working fluid are used for controlling said expansion valve.

15. The method according to claim 13, wherein the working fluid is also examined between the evaporator and the compressor.

16. The method according to claim 11, wherein the examined fluid is a liquid in a vaporizer, and is examined in at least one level therein to indicate the liquid level in the vaporizer.

17. The method according to claim 11, wherein the examined fluid is examined for its chemical composition.

18. The method according to claim 11, wherein the fluid is first examined while non-flowing or flowing at a known velocity to indicate its composition, and then is examined while flowing at an unknown velocity to indicate its velocity.

19. Apparatus for providing an indication of the composition of an examined fluid, comprising:

an electrical resistor having a mounting device for mounting the electrical resistor immersed in the fluid to be examined;

a power supply for supplying electrical current to the electrical resistor to heat it to a temperature above that of the examined fluid;

and a processor for: (a) controlling the heating current applied to the electrical resistor to maintain the electrical resistor substantially at a predetermined temperature; (b) measuring the electrical current applied to the electrical resistor to maintain it substantially at said predetermined temperature; and (c) producing an output, based on the measured electrical current, indicating the composition of the examined fluid.

20. The apparatus according to claim 19, wherein said electrical resistor is a positive temperature coefficient (PTC) thermistor.

21. The apparatus according to claim 20, wherein said mounting device includes a fitting attachable at one end to a housing containing the fluid to be examined and carrying said thermistor at the opposite end such as to immerse the thermistor in the fluid to be examined when the fitting is attached to said housing.

22. The apparatus according to claim 21, wherein said fitting further includes electrical circuitry connected to said thermistor for sensing the current flow through the thermistor, and electrical connections for connecting said circuitry and thermistor to the power supply.

23. The apparatus according to claim 20, in combination with a heat pump including a phase-changing working fluid driven through a closed-loop cycle, comprising a compressor, a condenser, an expansion valve, and an evaporator; said thermistor being immersed in the working fluid in at least one stage of said closed loop to indicate the relative proportions of the working fluid thereat in the liquid and vapor phases.

24. The apparatus according to claim 23, wherein said thermistor is immersed in the working fluid between the expansion valve and the evaporator.

25. The apparatus according to claim 24 wherein said processor also controls said expansion valve in response to the measured liquid-vapor proportions of the working fluid between the expansion valve and the evaporator.

26. The apparatus according to claim 23, wherein said thermistor is immersed in the working fluid between the evaporator and the compressor.

27. The apparatus according to claim 23, wherein a thermistor is immersed in the working fluid between the expansion valve and the evaporator, and another thermistor is immersed in the working fluid between the evaporator and the compressor.

28. The apparatus according to claim 20, in combination with a liquid vaporizer for vaporizing a liquid, said thermistor being introduced in the vaporizer to indicate the liquid level therein.

* * * * *